US007909981B2

(12) United States Patent
Dalmia

(10) Patent No.: US 7,909,981 B2
(45) Date of Patent: Mar. 22, 2011

(54) METHOD AND APPARATUS FOR IMPROVING THE PERFORMANCE OF AN ELECTROCHEMICAL SENSOR

(75) Inventor: Avinash Dalmia, Hamden, CT (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 1034 days.

(21) Appl. No.: 11/070,299

(22) Filed: Mar. 2, 2005

(65) Prior Publication Data
US 2005/0194264 A1 Sep. 8, 2005

Related U.S. Application Data

(60) Provisional application No. 60/521,171, filed on Mar. 3, 2004.

(51) Int. Cl.
G01N 27/38 (2006.01)
(52) U.S. Cl. .......................... 205/705; 205/687; 205/775
(58) Field of Classification Search .................. 205/687, 205/775, 650
See application file for complete search history.

(56) References Cited

U.S. PATENT DOCUMENTS

| 4,508,598 A | * | 4/1985 | Giner | ........................ 205/782.5 |
| 4,939,924 A | * | 7/1990 | Johnson et al. | ............... 73/61.52 |
| 5,431,806 A | | 7/1995 | Suzuki et al. | |
| 5,478,460 A | | 12/1995 | Sugama et al. | |
| 5,492,611 A | | 2/1996 | Sugama et al. | |
| 5,670,031 A | | 9/1997 | Hintsche et al. | |
| 6,129,824 A | * | 10/2000 | Rollick et al. | ................. 204/412 |
| 6,413,398 B1 | * | 7/2002 | Gerhardt et al. | ............... 204/452 |
| 2001/0033805 A1 | * | 10/2001 | Jacobs et al. | ....................... 422/3 |

FOREIGN PATENT DOCUMENTS

| EP | 0361810 A2 | | 4/1990 |
| EP | 0887641 A1 | * | 12/1998 |
| WO | WO 03/098205 A1 | * | 11/2003 |

OTHER PUBLICATIONS

Examination Report from the European Patent Office, Application No. 05724809.8-2204, Jan. 15, 2009, 12 pages.

* cited by examiner

Primary Examiner — Ula C Ruddock
Assistant Examiner — J. Christopher Ball
(74) Attorney, Agent, or Firm — St. Onge Steward Johnston & Reens LLC

(57) ABSTRACT

The present teachings relate to systems and methods for oxidizing a sensor having a substrate, an electrode in contact with the substrate, and an electrolytic material in contact with the electrode, where oxidizing includes applying an oxidizing potential (between approximately 350 mV and 700 mV) to the electrode. In some embodiments, the methods and systems include hydrating the sensor by applying a hydrating potential (between approximately 0 mV and −500 mV) to the electrode. In some embodiments, the applied potential can vary cyclically between an oxidizing and hydrating potential.

20 Claims, 6 Drawing Sheets

Sensor Response After Regeneration at Fixed Potential(550mv) for 1 hr

METHOD AND APPARATUS FOR IMPROVING THE PERFORMANCE OF AN ELECTROCHEMICAL SENSOR

PRIOR APPLICATION

Applicant claims priority benefits under 35 U.S.C. §119(e) of U.S. Provisional Patent Application Ser. No. 60/521,171 filed Mar. 3, 2004, the contents of which are herein incorporated by reference in their entirety.

FIELD OF THE INVENTION

The invention relates to a method for improving sensitivity and response time for an electrochemical gas sensor.

BACKGROUND OF THE INVENTION

Electrochemical gas sensors are typically used to determine the composition of a gas and may further be used to detect the presence of various elements or compounds in a gas. Electrochemical sensors ordinarily operate at room temperature, provide a signal which varies with concentrations of analyte species, have short response time, and exhibit acceptable sensitivity with high durability. In addition, electrochemical sensors are compact and can be used for continuous monitoring.

Known electrochemical sensors include, using both liquid and solid electrolytic layers, capacitance sensors and surface acoustic wave sensors. However, the sensitivity, or detection capability, of known sensors generally falls in the range of low-ppm or high-ppb.

Other known electrochemical gas sensors typically include gas diffusion electrodes and porous electrolytic films of, for example, Nafion or Teflon. The cornerstone of these sensors generally has been on optimizing the metal/gas/ionic medium interface in order to achieve higher sensitivity. However, the assembly processes for these sensors are manually intensive and are not suited for automated mass production.

U.S. Pat. No. 5,431,806 ("806 patent"), U.S. Pat. No. 5,492,611 ("611 patent"), and U.S. Pat. No. 5,478,460 ("460 patent") disclose an electrochemical gas sensor having a permeable membrane. These types of sensors typically measure gas by diffusing it through the membrane and dissolving it in an electrolyte on the other side of the membrane. The electrolyte is in contact with electrodes, which in turn typically measure current flow as a function of oxygen concentrations.

U.S. Pat. No. 5,670,031 ("031 patent") is directed to an electrochemical sensor having a plurality of micro electrodes in series and in close proximity to one another. This sensor typically operates by measuring differences in current flow between one pair of electrodes to the next along a length of a channel in which electrolyte flows. Because minute changes in current flow can be measured, accuracy is generally believed to be improved.

Regardless of the type of electrochemical sensor selected, many typically suffer reduced response time or reduced sensitivity over time. This may occur through simple use of the sensor. Usually after each use, the inside surfaces of electrochemical sensors, particular the sensing electrode, may become coated with impurities. Such impurities include oxidation and may result from the reaction between the gas, electrolytic membrane, electrode surface which is typically metallic, and/or electricity or current. The more the sensor is used and if the sensor is not cleaned, such impurities may lead to corrosion of the electrode surface. Moreover, as impurities, corrosion, or oxidation build up on the surfaces of the sensor's components, sensitivity or sensor response time may be negatively affected.

Typically, ex-situ cleansing of the components' surfaces would usually remove or reduce the above listed impurities, which would often lead to improved sensitivity and response time. However, ex-situ cleansing, which normally involves the removal of the components or dismantling of the sensor, may be time consuming and expensive since these components may require careful handling and an environment free from airborne particles.

SUMMARY OF THE INVENTION

The present teachings include methods and systems to enhance sensor performance by reducing impurities within the sensor, which can be performed by cleaning the sensor without dismantling the sensor. Also included are method and systems for oxidizing the surface of the electrode without disassembling the sensor. Yet further are methods and systems for hydrating a sensor's electrolytic material without disassembling the sensor.

Some embodiments are methods and systems for cyclically varying between a potential applied to the electrode for oxidizing the surface of the electrode and a potential applied to the electrode for generating moisture.

More particularly, the invention relates to a method for oxidizing a sensor that has a substrate, an electrode in contact with the substrate, and an electrolytic material in contact with the electrode by applying an oxidizing potential to the electrode where the oxidizing potential is between approximately 350 mV and approximately 700 mV.

In some aspects of the method, applying an oxidizing potential includes determining a time for applying the oxidizing potential based on at least one measurement of a concentration of impurity before applying the oxidizing potential and a concentration of impurity after applying the oxidizing potential.

In other aspects of the method, applying an oxidizing potential includes applying it for a time duration such that the concentration of impurity after applying the oxidizing potential is less than approximately ten percent of the concentration of impurity before applying the oxidizing potential. In some of these aspects, applying the oxidizing potential includes applying it for a time duration such that the concentration of impurity after applying the oxidizing potential is less than approximately one percent of the concentration of impurity before applying the oxidizing potential. In further aspects, the oxidizing potential is applied for approximately one hour.

The method may include determining a measuring potential at which a concentration of a gas component is determined and selecting the oxidizing potential to be an increased potential when compared to the measuring potential. In some of these aspects, the method includes hydrating the sensor by applying a hydrating potential, where the hydrating potential is a lower potential than the measuring potential. In further aspects, applying the hydrating potential comprises determining a time for applying the hydrating potential, the time based on an amount of water and charge.

In an embodiment, the invention relates to a method for hydrating a sensor that has a substrate, an electrode in contact with the substrate, and an electrolytic material in contact with the electrode by applying a hydrating potential to the electrode where the hydrating potential is between approximately 0 mV and approximately −500 mV.

In some aspects, applying a hydrating potential includes determining a time for applying the hydrating potential based on at least one measurement of an amount of moisture held by the electrolytic material before applying the hydrating potential and an amount of moisture held by the electrolytic material after applying the hydrating potential.

In other aspects of the method, applying a hydrating potential includes applying it for a time duration such that the amount of moisture after applying the hydrating potential is less than approximately twenty percent of the weight of the electrolytic material. In some of these aspects, applying the hydrating potential includes applying it for a time duration such that the amount of moisture after applying the hydrating potential is more than ten percent of the weight of the electrolytic material. In further aspects, the hydrating potential is applied for approximately one hour.

The method may include applying a hydrating potential to include determining a measuring potential at which a concentration of a gas component is determined and selecting the hydrating potential to be a lowered potential when compared to the measuring potential. In some of these aspects, the method includes oxidizing the sensor by applying an oxidizing potential, where the oxidizing potential is a higher potential than the measuring potential. In further aspects, applying the oxidizing potential comprises determining a time for applying the oxidizing potential, the time based on a concentration of impurity before and after applying the oxidizing potential.

In a further embodiment, the invention relates to a method for oxidizing and hydrating a sensor having a substrate, electrode in contact with the substrate, and an electrolytic material in contact with the electrode. The method includes establishing a measuring potential used to determine a concentration of a gas component in a mixture of gases, applying an oxidizing potential to the electrode that is above the measuring potential, and applying a hydrating potential to the electrode that is below the measuring potential. In this embodiment, the method includes oxidizing and hydrating the electrode without disassembling the sensor.

In some aspects of this embodiment, the method cyclically varies the potential between the oxidizing potential and the hydrating potential.

In other aspects, the method includes removing impurities from the electrode without disassembling the sensor. In further aspects, the method maintains a generally consistent potential above the measuring potential for reducing impurities. In still other aspects, the method cyclically applies the measuring potential to the electrode to determine if a variance between applications indicates a reduction of impurities.

DETAILED DESCRIPTION OF THE DRAWINGS

Figure 1:
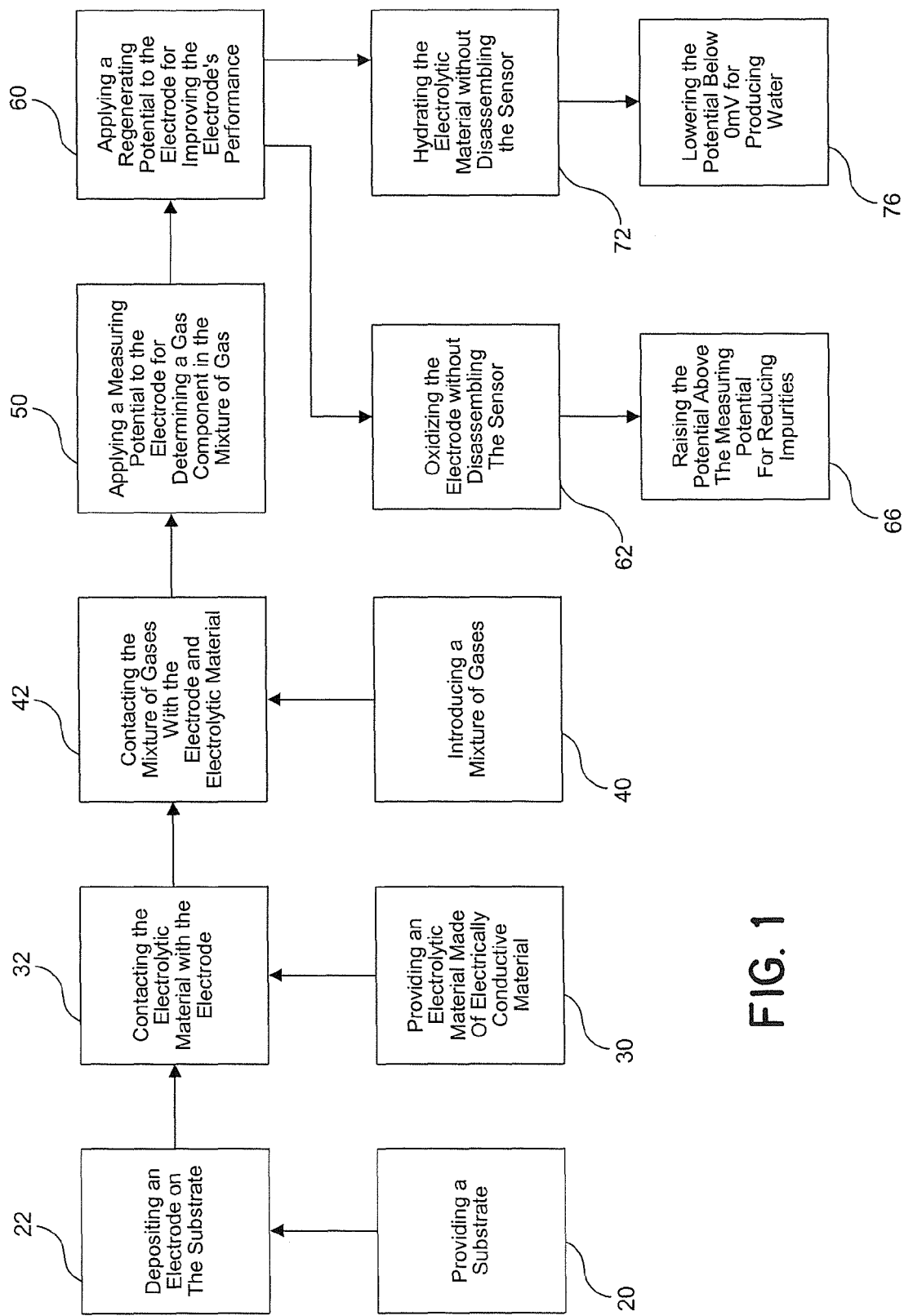
FIG. 1 depicts a method for oxidizing an electrode and hydrating an electrolytic material of a sensor.

FIG. 1 depicts a method 10 in accordance with the present teachings. Method 10 includes providing 20 a substrate made of an insulative material and depositing 22 an electrode on the substrate. Method 10 also includes providing 30 an electrolytic material made of electrically conductive material and contacting 32 the electrolytic material with the electrode. Method 10 further includes introducing 40 a mixture of gases into a sensor containing the substrate, electrolytic material, and electrode and contacting 42 the mixture of gases with the electrode and electrolytic material. In this fashion, there is a 3 phase contact point between gas, electrode, and electrolytic material so that gas detection may be enhanced.

Over time, gas impurities build up on the electrode surface that may negatively affect gas detection. Impurities include corrosion and/or oxidation build up. Method 10 can improve gas detection by reducing these impurities, for example, by affecting the sensor's performance.

Electrochemical sensors can benefit from at least a partial restoration when they get exposed or contaminated with organic or other impurities. These impurities can be at least partially removed by oxidizing them at the surface. The amount of time required to restore the surface by removing and/or reducing impurities depends on the type and amount of impurity and electrode potential. Another way to recognize whether a sensor is fully regenerated is to determine whether the sensor baseline (after you apply a fixed potential) changes by no more than 10% over 10 seconds. If the user is cycling the potential, then for full regeneration, two consecutive voltammograms should be within 5% of each other. As used herein, regeneration can be understood to include a restoration of sensor performance, which can include at least a partial restoration of sensor performance, when compared to a sensor without corrosion or oxidation buildup.

Figure 3:
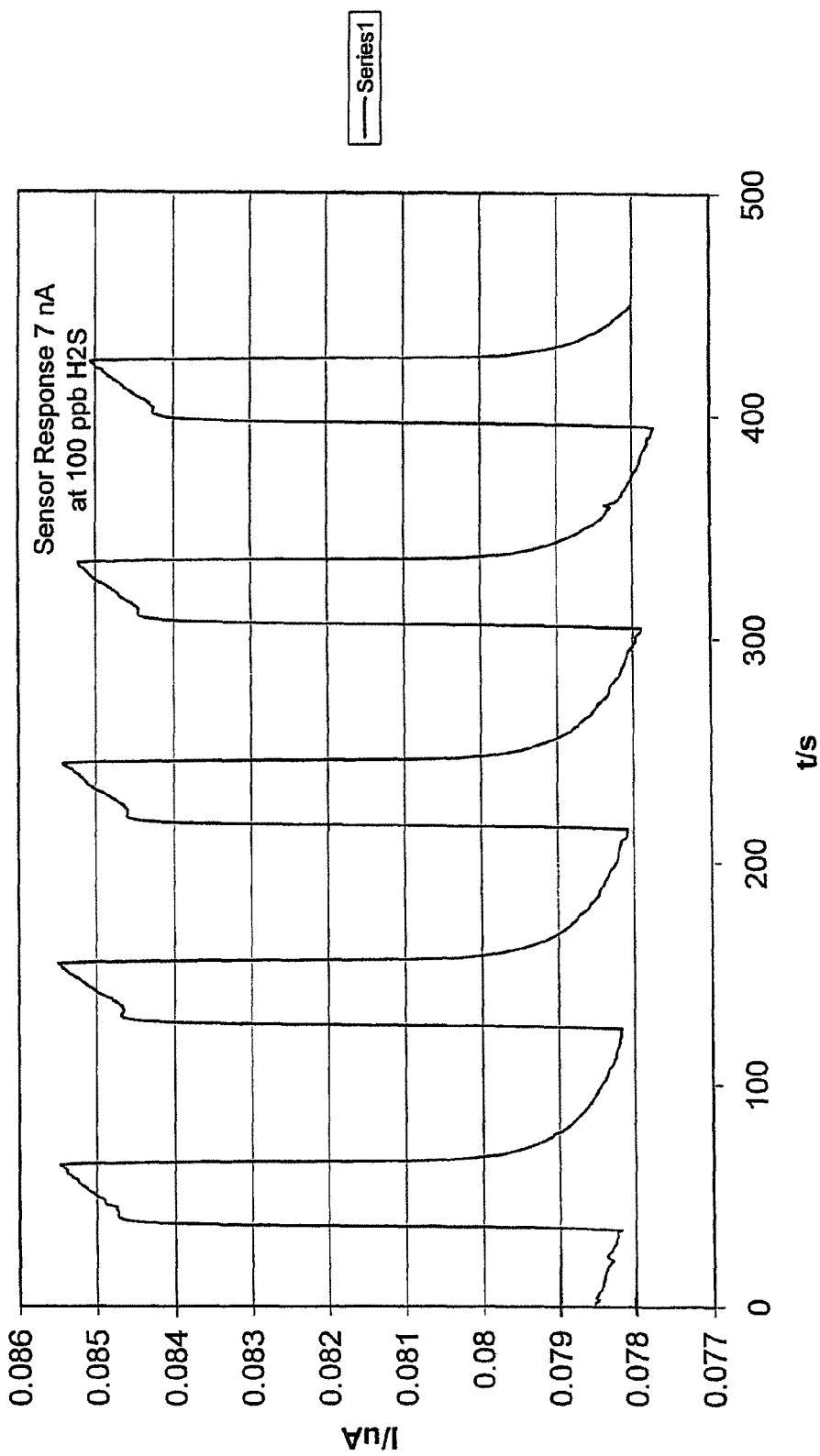
FIG. 3 depicts a response from a sensor before regeneration.
Figure 4:
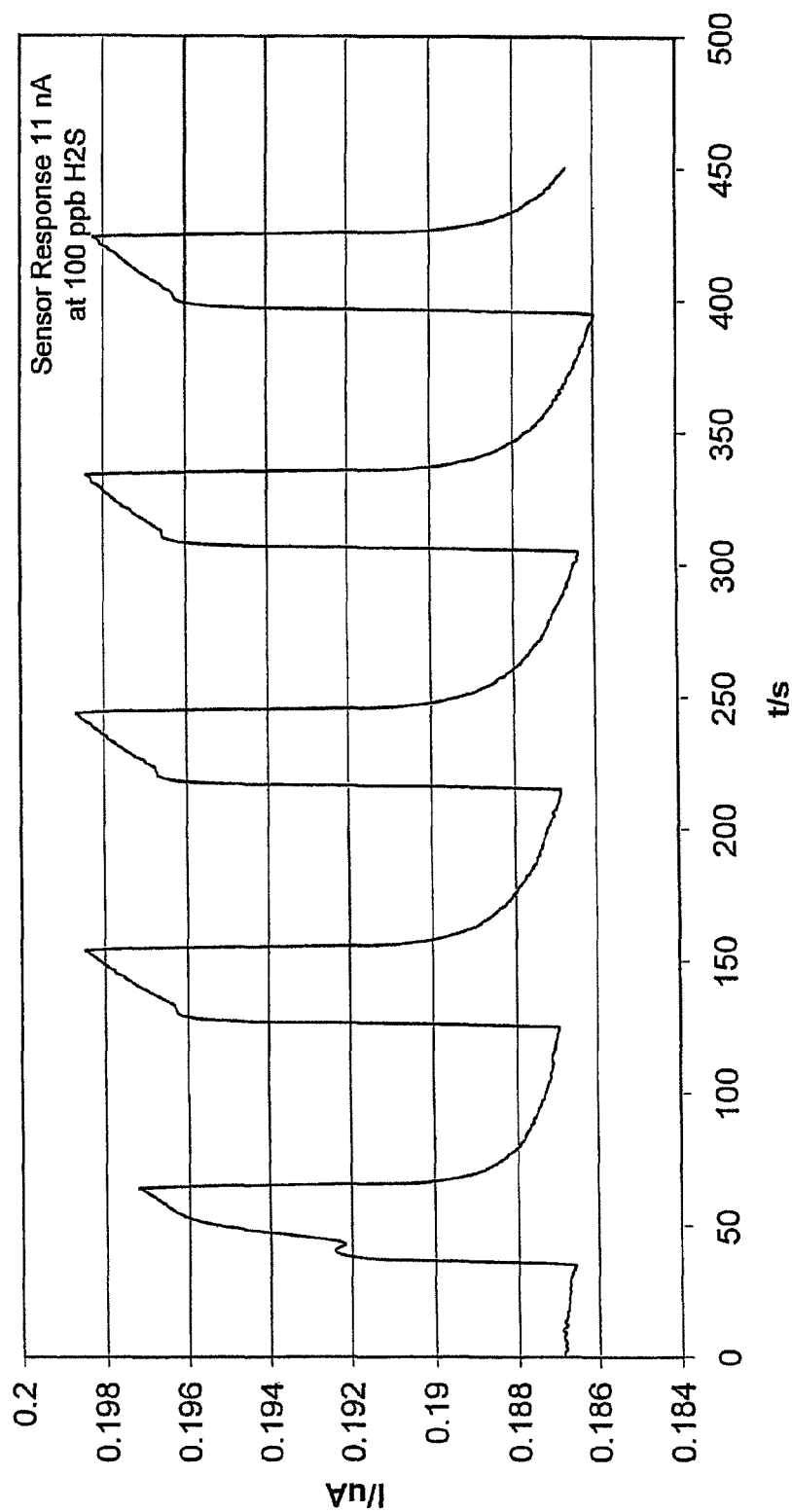
FIG. 4 depicts a response from the sensor of FIG. 3 after regeneration.
Figure 5:
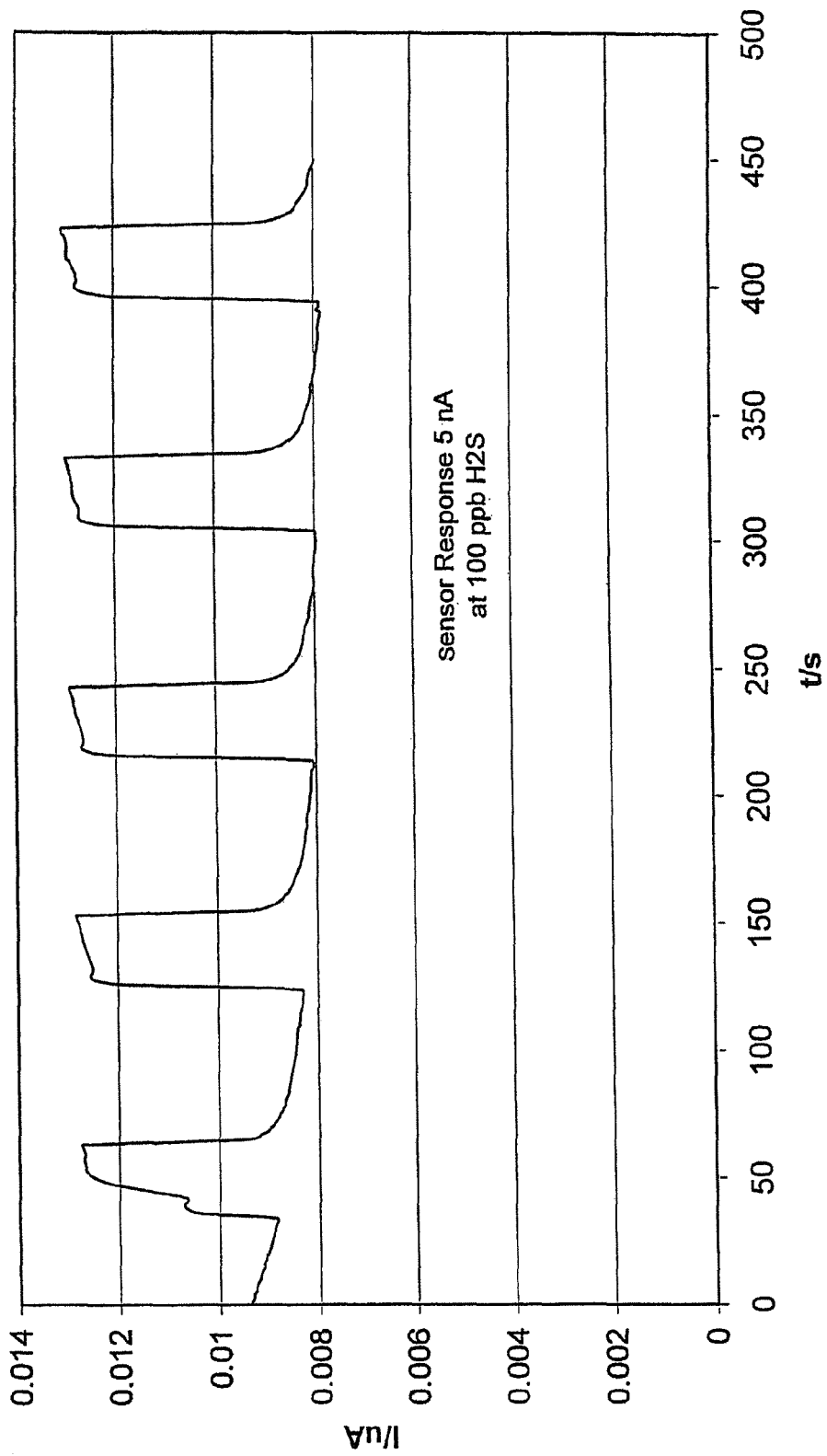
FIG. 5 depicts another response from a sensor before regeneration.
Figure 6:
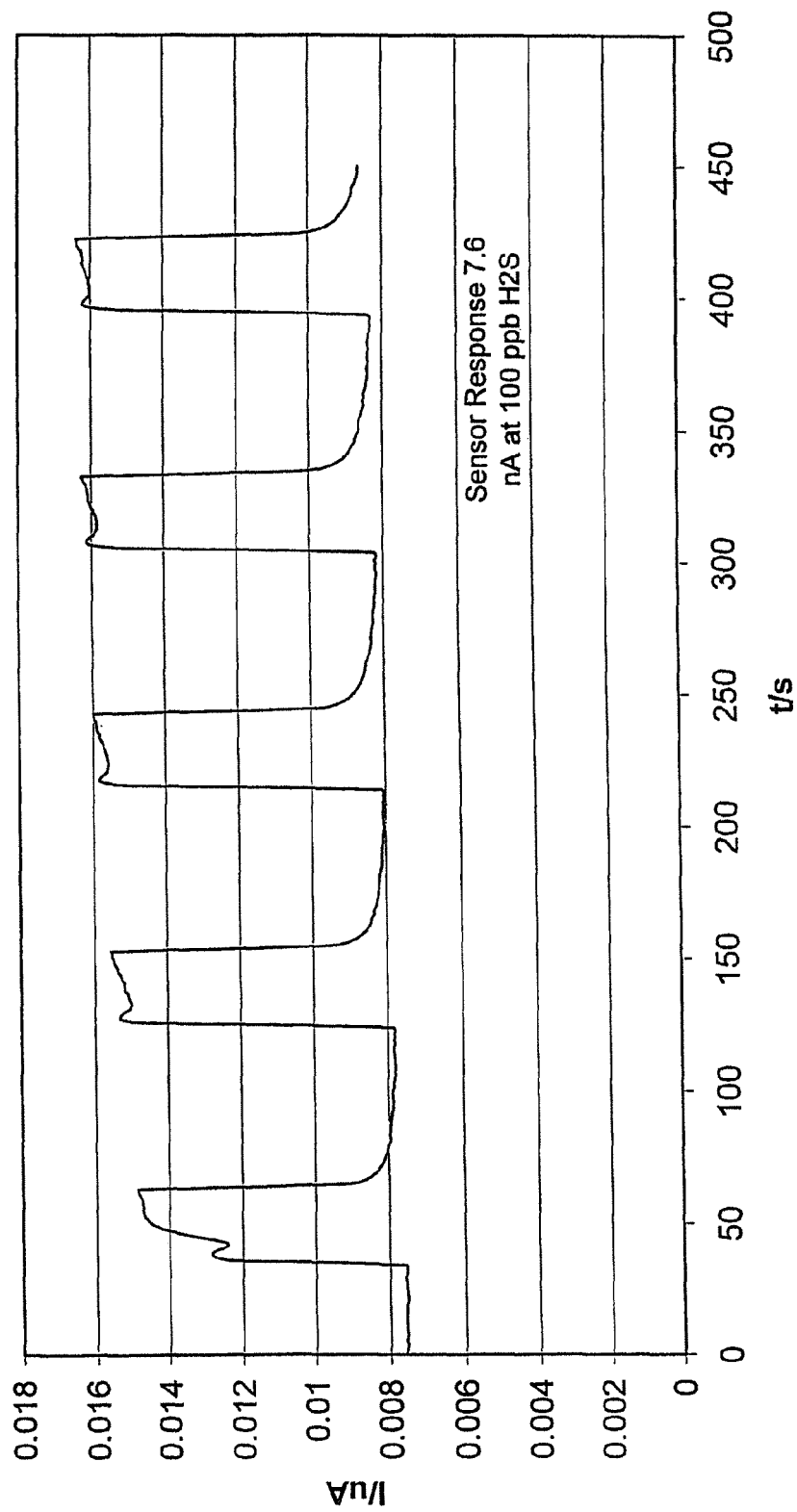
FIG. 6 depicts a response from the sensor of FIG. 5 after regeneration.

FIGS. 3 and 5 depict responses from a sensor before regeneration. FIG. 4 depicts a response of the sensor of FIG. 3 after regeneration by cyclically varying the potential between about −0.500 mV and about +600 mV for about one hour. FIG. 6 depicts a response of the sensor of FIG. 5 after regeneration by maintaining a fixed potential of about 550 mV for about one hour. As shown by FIGS. 4 and 6, sensor performances are improved relative to the baseline established and shown in the sensor measurements of FIGS. 3 and 5, respectively. Moreover, the improved and/or regenerated sensor performances are achieved without disassembling the sensors.

It should be known that the sensor measured in FIG. 3 is different from the sensor measured in FIG. 5. Theoretically, had the same sensors been used in both measurements, FIGS. 3 and 5 would be similar or identical. However, the improvement in sensor performance that is graphically shown by the relative differences between FIGS. 3 and 4 and between 5 and 6 would still be as shown, although the numerical values of the current and time may change.

Returning to FIG. 1, method 10 regenerates the sensor's performance by oxidizing 62 the electrode and/or by hydrating 72 the electrolytic material, where such oxidizing and hydration can be performed without sensor disassembly. The following principles guide the oxidation and hydration theories for regenerating a sensor:

At Positive Potential: Oxidation of Organic Impurities

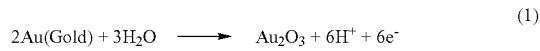

$$2\text{Au}(\text{Gold}) + 3\text{H}_2\text{O} \longrightarrow \text{Au}_2\text{O}_3 + 6\text{H}^+ + 6e^- \quad (1)$$

$$\text{CH}_3\text{OH}(\text{Alcohol Impurity}) + \text{Au}_2\text{O}_3 \longrightarrow \text{CO}_2 + 2\text{H}_2\text{O} + \text{Au} \quad (2)$$

At Negative Potential: Hydration of Membrane by Oxygen reduction $$O_2 + 4H^+ + 4e^- \longrightarrow 2H_2O \quad (3)$$

These potentials, referred to herein as oxidizing and hydrating potentials, are measured with respect to a gold/air or a platinum/air reference electrode. These potentials will vary if the material for the reference electrode and, to a lesser extent, the sensing electrode, changes.

After establishing a measuring a potential, which is the potential at which readings are taken to ascertain a concentration of a gas in a mixture of gases, the illustrated method 10 of FIG. 1 includes increasing 66 the potential of the electrode above the measuring potential, where such increase in electrode potential allows for reducing impurities (e.g., oxidizing potential). The raised oxidizing potential is high enough such that oxidation occurs but not so high that water is consumed, in which case the electrode may be damaged or suffer other negative effects. Since equation (3) is the equation for hydration, then the reverse of equation (3) would indicate a formula for oxidation.

$$2H_2O \longrightarrow O_2 + 4H^+ + 4e^- \quad (4)$$

The highest empirically determined potential to reduce impurities is approximately 700 mV. At potentials higher than approximately 700 mV, water would be consumed to a large extent and electrode damage may occur. Accordingly, the present teachings include embodiments with potentials between approximately 400 mV and approximately 650 mV, and more in some embodiments based on experimental data, potentials between approximately 500 mV and approximately 600 mV.

For the disclosed methods and systems, the raised oxidizing potential can be substantially held and/or maintained for a time determined by:

$$t = V\delta(Ln(Cin/Cfi))/DA \quad (5)$$

where t is time
V is volume of electrolyte
δ is polymer electrolyte thickness
Cin is initial concentration of impurity
Cfi is the final concentration of impurity (is about 1-10% of Cin)
D is diffusion coefficient of impurity
A is the area of cross-section of sensing electrode Since equation (5) relates Cin and Cfi by a ratio, the values of Cin or Cfi are not critical provided the final concentration of Cfi to Cin is approximately 1/100-10/100, or 1-10%. It is understood the removal of impurities increases as the concentration of Cfi to Cin approaches zero percent, Hence a ratio of Cfi/Cin of 1/1000, or 0.1%, would result in a further reduction in impurities than a 1% ratio, and sensor regeneration would be improved for the former case. However, better sensor regeneration may result in a longer exposure time to the aforementioned increased or raised oxidizing potential. Time t could be increased in order to arrive at 1% as compared to 10% and time t would further be increased in order to arrive at 0.1% as compared to 1%. A shorter time t may be achieved but the amount of impurities that are reduced would be compromised. For some embodiments, experimental determinations indicate that a ratio of approximately 1-10% generally yields acceptable impurity reduction.

Hydrating 72 the electrolytic material includes lowering 76 the potential applied to the electrode for a time determined by the following formula in order to generate water at the electrode's surface ("hydrating potential"), in which case the electrolytic material would absorb this water since it is in contact with the electrode:

$$Qreq = WnF/MW \quad (6)$$

W is the amount of water required in grams.
Qreq is the charge required.
n is number of electrons required per molecule of water formed is 2 in this case from equation.
F is a Faraday's constant=96,500 coulombs/equivalent
MW is molecular weight of water (18 in this case).

The amount of water W is calculated based on the surface area and thickness of the electrolytic material. Once the volume of the electrolytic material is calculated, the weight of the electrolytic material may be determined based on its known density. An estimate of the weight of water is thereafter determined to be approximately 10%-20% of the weight of the electrolytic material, where the approximate 10%-20% is a rule of thumb experimentally determined.

MW, F, and n are known constants, and thus Qreq can be determined and equated to Q measured, which is governed by the following equation, to solve for a hydration time: Qmeas=∫Idt.

Hence, integrating current I over time until Qmeas=Qreq provides a solution for hydration time t. Current I is known because it is applied by a user and is therefore known.

Figure 2:
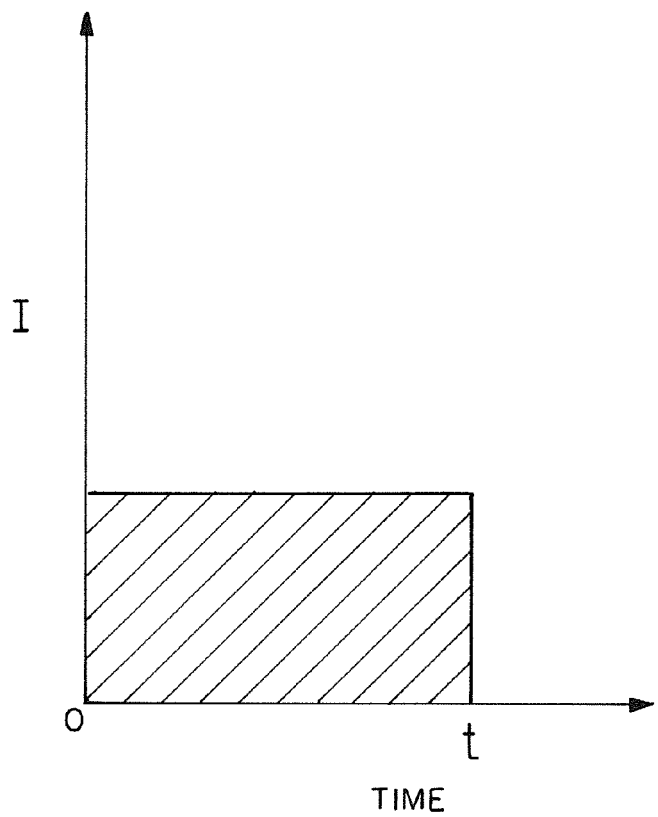
FIG. 2 depicts a manner for determining a time to hold the lower potential shown in FIG. 1.

As shown in FIG. 2, time t may be graphically determined by charting current I versus time t. As soon as the area (shaded) under the curve is equal to Qreq, the time at that point is time t.

In some embodiments, and unlike raising an electrode potential well above a measuring potential during oxidation, lowering an electrode potential well below the measuring potential does not introduce negative effects to the sensor. Lowering the electrode potential beyond a calculated lower or hydrating potential does not enhance hydration of the electrolytic material by creating more water at the contact between electrode and electrolytic material. Hydration at the calculated lower potential is the same as a potential well below the calculated lower hydrating potential.

Although further reducing a reduced electrode potential does not affect quantity of water, it can be understood that oversaturation, or flooding, may occur if the time for hydration is extended beyond the calculated hydration time t. As provided herein, excessive oxidation time does not adversely affect the sensor, while excessive hydration time may cause oversaturation. While increased oxidation time may lead to less impurities and improved sensor performance, increased hydration time may have an adverse affect on sensor performance.

The equations provided herein thus permit for a determination of an increased, or oxidizing potential, a time the increased potential is to be applied, a lowered or hydrating potential, and a time the lowered potential is to be applied. Moreover, it can be understood that an equilibrium potential is a potential at which no or negligible reaction takes place. For example, if a measuring potential for $H_2S$ is determined to be approximately 200 mV, and a raised potential is calculated to be between approximately 500 mV-600 mV, an equilibrium potential is between the raised potential and the measuring potential. For $H_2S$, this equilibrium potential can be approximately 300 mV. The raised/increased potential for oxidizing the electrode is above the approximate 300 mV equilibrium potential.

Similarly, if a lowered potential for $H_2S$ is determined to be approximately −500 mV, an equilibrium potential is between the lowered potential and the measuring potential. For $H_2S$, this can be approximately −100 mV. The lowered potential to hydrate the electrolytic material is below the approximate −100 mV equilibrium potential.

Hydration, or rehydration without disassembly, may be maintained at a substantially fixed potential. The amount of time required to rehydrate the membrane depends on the negative potential applied, oxygen concentration, thickness of polymer electrolyte, and hydration capacity of electrolyte. For example, if the membrane size is 1 sq.cm by 1 micron thickness, and if hydration capacity is approximately 10% by weight, the membrane can hold about 10% of its weight, which is approximately 0.1 mgm or approximately 100 microgm. If this membrane is substantially completely dry, then for rehydration process, the amount of water produced should be around 10 microgram. The amount of time to produce this amount of water can be calculated using equation (6).

In some embodiments, a method of determining a time to apply a raised (oxidizing) and/or lowered (hydrating) potential includes taking at least two consecutive measurements/readings across the sensing electrode, and if these two readings yield a value within 10% of each other over a measurement time period such as approximately 10 seconds or longer, oxidation and/or regeneration may be considered complete. If the readings are within 5% over 10 seconds or longer, this may indicate complete regeneration or oxidation.

It can be understood that not only may a potential be raised and substantially held for a first time t, and/or lowered and substantially held for a second time t, but in some embodiments, a potential may be cyclically varied between the raised, oxidizing potential and the lowered, hydrating potential. Cyclically varying the potential in a time period can oxidize and hydrate the sensor as opposed to oxidizing or hydrating. The total time required to sufficiently oxidize and/or hydrate are still governed by the above equations.

For the purposes of the present disclosure, "about" or "approximately" when referenced to potentials can include +/−50 mV.

In addition to or instead of calculating a time for oxidizing the electrode and/or hydrating the electrolytic material, a user may quickly determine if a sensor's performance has been adequately improved by taking at least two consecutive measurements across the electrode and if the variance, or difference, between the two measurements is small or negligible, then the electrode is sufficiently oxidized or the electrolytic material is sufficiently hydrated. For example, if the variance is less than approximately 10% over 10 seconds, or less than 5% over 5 seconds, oxidation and/or hydration may be sufficiently completed and, therefore, sensor performance may be enhanced. The variance and time between measurements vary depending upon the type of sensor measured, type of gas being detected, amount of impurity, and potential applied.

What is claimed is:

1. A method for cleaning an electrode in a sensor, the sensor comprising a substrate, the electrode in contact with the substrate, and an electrolytic material in direct contact with the electrode, the method comprising the steps of:
   determining a measuring potential at which a concentration of a gas component is determined;
   applying a hydrating potential, the hydrating potential being a lower potential than the measuring potential in order to hydrate the sensor;
   selecting an oxidizing potential that is greater than the measuring potential; and
   applying the oxidizing potential to the electrode, the oxidizing potential between approximately 451 mV and approximately 649 mV, wherein the step of applying an oxidizing potential comprises:
   determining a time for applying the oxidizing potential based on at least one measurement of:
      concentration of impurity before applying the oxidizing potential, and
      concentration of impurity after applying the oxidizing potential;
      wherein the sensor is cleaned without disassembling or dismantling the sensor, and
   wherein the step of applying an oxidizing potential further comprises taking at least two consecutive measurements across the electrode, wherein if these at least two consecutive measurements yield a value within 10% of each other over a measurement time period, oxidation and regeneration are considered complete.

2. The method of claim 1, where applying an oxidizing potential comprises:
   applying the oxidizing potential for a time duration such that the concentration of impurity after applying the oxidizing potential is less than approximately ten percent of the concentration of impurity before applying the oxidizing potential.

3. The method of claim 1, where applying an oxidizing potential comprises:
   applying the oxidizing potential for a time duration such that the concentration of impurity after applying the oxidizing potential is less than approximately one percent of the concentration of impurity before applying the oxidizing potential.

4. The method of claim 1, where applying an oxidizing potential comprises:
   applying the oxidizing potential for approximately one hour.

5. The method of claim 1, where applying the hydrating potential comprises:
   determining a time for applying the hydrating potential, the time based on an amount of water and charge.

6. A method for cleaning an electrode in a sensor, the sensor comprising a substrate, the electrode in contact with the substrate, and an electrolytic material in contact with the electrode, the method comprising:
   applying a hydrating potential to the electrode, the hydrating potential between approximately 0 mV and approximately −449 mV, wherein the step of applying the hydrating potential comprises:
   determining a time for applying the hydrating potential based on at least one measurement of:
      an amount of moisture held by the electrolytic material before applying the hydrating potential; and
      an amount of moisture held by the electrolytic material after applying the hydrating potential; and
   oxidizing the sensor;
   wherein the sensor is cleaned without disassembling or dismantling the sensor, and
   wherein the step of applying a hydrating potential further comprises taking at least two consecutive measurements across the electrode, characterized in that wherein if these at least two consecutive measurements yield a value within 10% of each other over a measurement time period, oxidation and regeneration are considered complete.

7. The method of claim 6, where applying the hydrating potential comprises:
applying the hydrating potential for a time duration such that the amount of moisture after applying the hydrating potential is less than approximately twenty percent of the weight of the electrolytic material.

8. The method of claim 6, where applying the hydrating potential comprises:
applying the hydrating potential for a time duration such that the amount of moisture after applying the hydrating potential is more that approximately ten percent of the weight of the electrolytic material.

9. The method of claim 6, where applying the hydrating potential comprises applying the hydrating potential for approximately one hour.

10. The method of claim 6, where applying the hydrating potential includes:
determining a measuring potential at which a concentration of a gas component is determined; and,
selecting the hydrating potential to be a lowered potential when compared to the measuring potential.

11. The method of claim 6, where oxidizing the sensor comprises:
applying an oxidation potential, the oxidation potential being a higher potential than the measuring potential.

12. The method of claim 11, where applying the oxidation potential comprises:
determining a time for applying the oxidation potential, the time based on a concentration of impurity before applying the oxidation potential and a concentration of impurity after applying the oxidation potential.

13. A method for oxidizing and hydrating a sensor, the sensor comprising a substrate, an electrode in contact with the substrate, and an electrolytic material in contact with electrode, the method comprising:
establishing a measuring potential used to determine a concentration of a gas component in a mixtures of gases;
applying an oxidizing potential to the electrode, the first oxidizing potential being above the measuring potential;
applying a hydrating potential to the electrode, the hydrating potential being below the measuring potential;
hydrating the electrolytic material; and
removing impurities from the electrode, wherein said steps are done without disassembling the sensor,
wherein the steps of applying an oxidation potential and applying a hydrating potential further comprise taking at least two consecutive measurements across the electrode, characterized in that wherein if these at least two consecutive measurements yield a value within 10% of each other over a measurement time period, oxidation and regeneration are considered complete.

14. The method of claim 13, further comprising oxidizing the electrode without disassembling the sensor.

15. The method of claim 13, further comprising hydrating the electrolytic material without disassembling the sensor.

16. The method of claim 13, further comprising cyclically varying the potential between the oxidizing potential and the hydrating potential.

17. The method of claim 13, further comprising maintaining a generally consistent potential above the measuring potential for reducing impurities.

18. The method of claim 13, further comprising cyclically applying the measuring potential to the electrode to determine if a variance between the cyclical applications indicates a reduction of impurities.

19. The method of claim 1, wherein said substrate is made of an insulative material.

20. The method of claim 16, wherein the potential is varied for about one hour.

* * * * *